United States Patent [19]
Conway-Myers et al.

[11] Patent Number: 5,837,543
[45] Date of Patent: Nov. 17, 1998

[54] HUMAN EMBRYO CO-CULTURE SYSTEM AND USES THEREOF

[75] Inventors: Barbara-Ann Conway-Myers, Helena; Michael P. Steinkampf, Bimingham, both of Ala.

[73] Assignee: UAB Research Foundation, Birmingham, Ala.

[21] Appl. No.: 861,888

[22] Filed: May 22, 1997

Related U.S. Application Data

[63] Continuation-in-part of Ser. No. 409,650, Mar. 24, 1995, abandoned.

[51] Int. Cl.$^6$ ............................ C12N 5/00; A61B 17/435; A61D 7/00
[52] U.S. Cl. ............................ 435/373; 435/366; 435/378; 435/404; 435/406; 600/33; 600/34
[58] Field of Search ...................................... 435/366, 373, 435/378, 404, 406; 600/33, 34

[56] References Cited

U.S. PATENT DOCUMENTS 5,213,979   5/1993   First et al. ............................... 435/373

OTHER PUBLICATIONS

Bongso and Fong. Current Opinion in Obstet. and Gyn. vol. 5, pp. 585–593, 1993.
Bongso et al. Human Reprod. vol. 8 (8), pp. 1155–1162, 1993.
Bongso et al., Human Reprod. vol. 4 (5), pp. 486–494, 1989.
Henriksen et al. Human Reprod. vol. 5 (1), pp. 25–31, 1990.
Irvine Scientific —Manufacturer's Brochure, 1993.
Hycor Scientific —Manufacturer's Brochure, 1994.

*Primary Examiner*—Leon B. Lankford, Jr.
*Assistant Examiner*—Christopher R. Tate
*Attorney, Agent, or Firm*—Benjamin Aaron Adler

[57] ABSTRACT

The present invention provides a human embryo co-culture system comprising a suspension of cultured human tubal epithelial cells. Also provided is a method of method of improving the pregnancy rate of a female undergoing in vitro fertilization, comprising the steps of: contacting an oocyte from said female with a monolayer of cultured human tubal epithelial cells; inseminating the oocyte; and transferring an embryo back to said female.

12 Claims, 4 Drawing Sheets

HUMAN EMBRYO CO-CULTURE SYSTEM AND USES THEREOF

CROSS-REFERENCE TO RELATED APPLICATION

This application is a continuation in part of U.S. Ser. No. 08/409,650, filed Mar. 24, 1995, now abandoned.

BACKGROUND OF THE INVENTION

1. Field of the Invention

The present invention relates generally to the fields of reproductive gynecology and biochemistry. More specifically, the present invention relates to a novel human embryo co-culture system to improve human embryo growth in vitro and, consequently, increase pregnancy rates in infertile women undergoing in vitro fertilization (IVF) treatment.

2. Description of the Related Art

Under normal conditions in the human female, a single follicle is selected from a cohort of follicles to mature, and after the Luteinizing Hormone (LH) surge, completes maturation and ovulates. The mature follicle releases an ova which is captured by the fimbria of the Fallopian tube and is available to be fertilized in the ampullar segment if sperm are present. After fertilization, the embryo continues to grow and develop as it passes through the remainder of the Fallopian tube. After 5 days of growth and development, the embryo, now a blastocyst, will hatch from the zona pellucida and implant within the wall of the uterus.

In vitro fertilization is a powerful and widely used technique for the treatment of infertility. In this procedure, human eggs are retrieved and mixed with sperm in a culture dish to allow fertilization. After two or three days of incubation, the embryos are transferred back to the patient. This technique is used for women with, for example, damaged or absent Fallopian tubes, endometriosis, male factor infertility and unexplained infertility. Over 30,000 in vitro fertilization cycles are performed in the United States and Canada annually. However, less than 20% of embryo transfers after in vitro fertilization result in a birth of a child. This is primarily due to the limitations of the in vitro culture system. Fertilization and early embryo development normally occur in the Fallopian tube. However, the Fallopian tube is more than a conduit between the ovary and the uterus. The Fallopian tube supplies a complex mixture of nutrients and may help to detoxify metabolic products produced by the embryo.

Despite the increasing use of in vitro fertilization as a treatment for infertility, the optimal system for preimplantation human embryo culture has not yet been determined. Although less than 20% of embryo transfers after in vitro fertilization result in birth, pregnancy rates in livestock animals with embryo transfer after in vivo fertilization exceed 60%, suggesting that early embryo events may be critical for subsequent conception after embryo transfer. Similarly, the improved pregnancy rates observed with gamete intra-Fallopian transfer, in which human gametes are incubated in vivo, suggest that the Fallopian tube may be more than a conduit for the preimplantation embryo, but rather may provide a source of complex nutrients or detoxify metabolic products produced by the embryo itself.

The prior art is deficient in an accurate determination of the optimal conditions for the harvesting and development of the tubal cell monolayers, for example, optimum serum concentration of culture medium during the preparation of human tubal monolayers which affects the proportion of epithelial cells obtained for subsequent use in embryo coculture. The present invention fulfills this longstanding need and desire in the art.

SUMMARY OF THE INVENTION

The present invention is directed to improving in vitro fertilization results by culturing early stage embryos on a monolayer of somatic cells. This embryo co-culture technique facilitates pre-implantation development and increases implantation rates in a variety of mammalian species, including humans. Although a number of cell types have been shown to be beneficial, the use of epithelial cells obtained from human Fallopian tubes most closely simulates the circumstances in which early embryonic development occurs. The optimal conditions for the harvesting and development of the tubal cell monolayers remain obscure. This information is critical for development of a co-culture system, since the overgrowth of non-epithelial elements derived from the oviductal tissue may not provide the equivalent beneficial effects on embryo growth.

The present invention demonstrates, inter alia, that low serum culture conditions enhance epithelial cell growth and development while higher serum concentrations favor fibroblast growth. The interaction between tubal epithelial cells and gametes plays a key role in the development of the pre-implantation embryo. Co-culture of tubal cells with pre-implantation embryos improves the success of in vitro fertilization treatment. However, the optimal conditions to establish epithelial cell co-culture have never been established. The present invention demonstrates the effect of serum supplementation on in vitro tubal cell growth and development. While the addition of serum facilitates growth of human tubal cells, a lower concentration of fetal calf serum favors the growth of epithelial cells over fibroblasts. This enhancement of epithelial cell development plays an important role in the effectiveness of embryo co-culture for in vitro fertilization.

In one embodiment of the present invention, there is provided a human embryo co-culture system comprising a suspension of cultured human tubal epithelial cells.

In another embodiment of the present invention, there is provided a method of improving the pregnancy rate of a female undergoing in vitro fertilization, comprising the steps of: contacting an oocyte from said female with a monolayer of cultured human tubal epithelial cells; inseminating the oocyte; and transferring an embryo back to said female.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows that the Fallopian epithelial cells stain positively for cytokeratin (Dark Arrow). Non-epithelial cells do not stain positively with cytokeratin (Open Arrow).

DETAILED DESCRIPTION OF THE INVENTION

Figure 1:
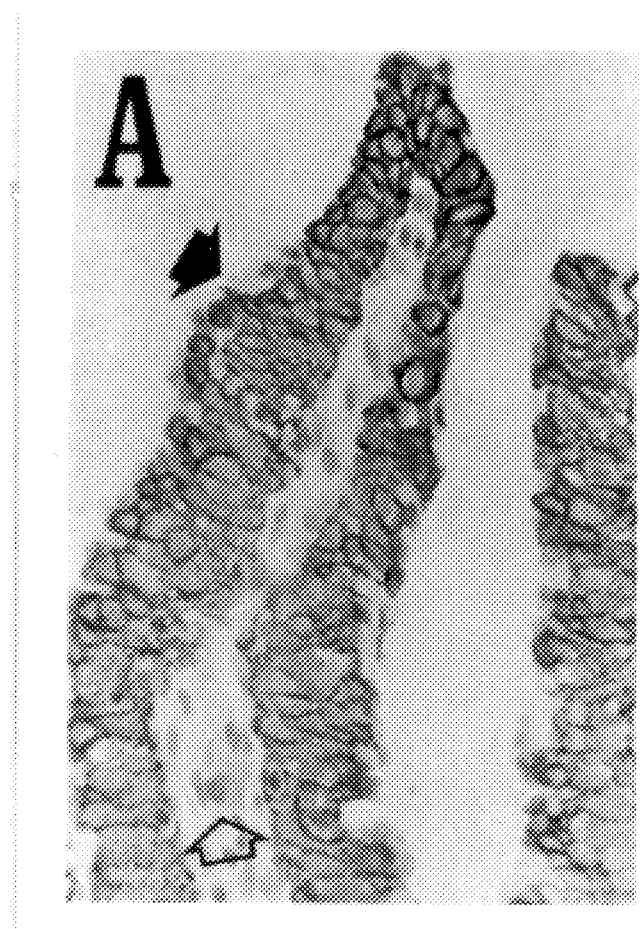
FIG. 1 shows the immunohistochemical staining of a human Fallopian tube (400×).

The present invention is directed to a human embryo co-culture system comprising a suspension of cultured human tubal epithelial cells. In a preferred embodiment of the present invention, the human embryo co-culture system is a frozen suspension.

In one embodiment of the present invention, the tubal epithelial cells are cultured by the steps of: culturing ampullary cells in a container holding a first medium until about 40% to about 80% confluence; detaching said cells from the surface of said container; and resuspending said cells in a second medium with serum, antibiotics and antifungal agents and replating said cells until about 40% to about 80% confluence.

In a preferred embodiment of the present invention, in the human embryo co-culture system, the first medium is CHANG MEDIUM® supplemented with fetal calf serum, antibiotics and antifungal agents. Preferably, the cells are cultured until about 60% to about 70% confluence.

In the human embryo co-culture system of the present invention, the cells are detached from said container manually. Preferably, the cells are detached from said container chemically. Most preferably, the cells are detached from said container by treating said cells with trypsin.

In the human embryo co-culture system of the present invention, the second medium is PC-I™ medium. Preferably, the serum is selected from the group consisting of fetal calf serum, bovine serum and female donor serum. The fetal calf serum may be in a concentration of about 1% to about 10%. Preferably, fetal calf serum is in a concentration of about 5%.

In the human embryo co-culture system of the present invention, the human embryo co-culture system of claim 3, wherein said antibiotic is selected the group consisting of penicillin and streptomycin. Representative concentrations of such antibiotics are 100 IU/ml penicillin and 100 μg/ml streptomycin. A representative examples of antifungal agents is amphotericin B in a concentration of 0.25 μg/ml.

In a most preferred embodiment, the formulation of CHANG MEDIUM® A is as follows: $CaCl_2$ (anhyd): 116.6 mg/l; Biotin:0.0035 mg/l; $CuSO_4$ $5H_2O$: 0.0013 mg/l; D-Ca panthothenate: 2.24 mg/l; $Fe(NO_3)s$ $9H_2O$:0.05 mg/l; choline chloride: 8.98 mg/l; $FeSO_4$ $7H2O$: 0.417 mg/l; Folic Acid: 2.65 mg/l; KCL: 311.80 mg/l; i-inositol: 12..6 mg/l; $MgCl_2$: 28.64 mg/l; Niacineamide: 2.02 mg/l; $MgSO_4$: 148.84 mg/l; Pyridoxal HCL; 2 mg/l; HEPES: 3574.5 g/l; Riboflavin: 0.219 mg/l; NaCl: 6995.5 mg/l; Thiamine HCl: 2.17 mg/l; $NaHCO_3$: 1200 mg/l; Thymidine: 0.365 mg/l; $NaH_2PO_4$ $H_2O$: 62.50 mg/l; Vitamin B12: 0.68 mg/l; $Na_2HGPO_4$: 71.02 mg/l; Penicillin: 100 IU /ml; D-glucose: 3151.0 g/l; Ampicillin: 8 mg/l; $ZnSO_4$ $7H_2O$: 0.432 mg/l; Transferrin: 5 μg/ml; Na Hypoxanthine: 2.39 mg/l; Selenium: 20 nM; Linoleic Acid: 0.042 mg/l; Insulin: 10 μg/ml; Lipoic Acid: 0.105 mg/l; Triiodothyronine: 0.1 nM; Sodium Putrescine 2HCl: 0.081 mg/l; Glucagon: 1 μg/ml; Sodium Pyruvate; 110 mg/l; Hydrocortisone: 1 nM; L-Alanine: 4.45 mg/l; Testosterone: 1 nM; L-Arginine: 147.50 mg/l; Progesterone: 1 nM; L-Asparagine $H_2O$: 7.5 mg/l; Estradiol: 1 nM; L-Aspartic Acid: 6.65 mg/l; Amphotericin B: 0.25 μg/ml; L-Cystine HCL $H_2O$: 17.65 mg/l; Adenosine: 5 mg/l; L-Cystine 2HCl: 31.29 mg/l; Cytosine: 5 mg/l; L-Glutamic Acid: 7.35 mg/l; Guanosine: 5 mg/l; L-Glutamine: 781 mg/l; Uridine: 5 mg/l; Glycine: 18.75 mg/l; 2'Deoxyandenosine: 5 mg/l; L-Histidine: Hcl $H_2O$ 31.48 mg/l; 2' Deoxyxytidine HCl: 6 mg/l; L-Isoleucine: 54.47 mg/l; 2' Deoxyguanosine: 5 mg/l; L-Leucine: 59.05 mg/l; Thymidine: 5 mg/l; L-Lysine HCL: 91.25 mg/l; L-Methionine: 17.24 mg/l; L-Phenyalanine: 35.48 mg/l; L-Proline: 17.25 mg/l; L-Serine: 26.25 mg/l; L-Threonine: 53.45 mg/l; L-Tryptophan: 9.02 mg/l; L-Tyrosine 2Na $2H_2O$: 55.79 mg/l; L-Valine: 52.85 mg/l;

In a most preferred embodiment, the formulation of the PC-1™ medium is as follows: $CaCl_2$ (anhyd): 100 mg/l; Biotin: 0..2 mg/l; Nicotinic Acid: 0.5 mg/l; Ascobic Acid: 0.5 mg/l; Para-aminobenzoic Acid: 1.0 mg/l; Choline Chloride: 5 mg/l; Bacto-peptone: 600 mg/l; Folic Acid: 10 mg/l; KCl: 400 mg/l; i-insitol: 36 mg/l; Glutathione: 0.50 mg/l; Niacinamide: 0.5 mg/l; MgSO4: 97.67 mg/l; Pyridoxal HCL: 0.5 mg/l; Pyrodoxine HCL: 0.5 mg/l; Riboflavin: 0.219 mg/l ; NaCl: 6460 mg/l; Thiamine HCL: 0.2 mg/l; $NAHCO_3$: 2200 mg/l; D-Ca Panthothenate: 0.2 mg/l; $NaH_2PO_4H_2O$: 580 mg/l; Vitamin $B_{12}$: 2 mg/l; D-glucose: 3000.0 g/l; Penicillin: 100 IU/ml; L-Alanine: 13.9 mg/l; Amplicillin: 8 mg/l; L-Arginine HCl: 42.1 mg/l; Streptomycin: 100 μg/ml; L-Asparagine: 45 mg/l; FCS: 5%; L-Aspartic Acid: 20 mg/l; Amphotericin B: 0.25%; L-Cystine HCL $H_2O$: 31.5 mg/l; Adenosine: 5 mg/l; L-Hydroxyproline: 19.7 mg/l; Cytidine: 5 mg/l; L-Glutamic Acid: 22.1 mg/l; Guanosine: 5 mg/l; L-Glutamine: 200 mg/l; Uridine: 5 mg/l; Glycine: 7.5 mg/l; 2'Deoxyadenosine: 5 mg/l; L-Histidine HCl $H_2O$: 21 mg/l; 2'Deoxyguanosine-HCl: 6 mg/l; L-Isoleucine: 39.3 mg/l; 2'Deoxyguanosine: 5 mg/l; L-Leucine: 39.3 mg/l; Thymidine: 5 mg/l; L-Lysine: 36.5 mg/l; Lipoic Acid: 0.2 mg/l; L-Methionine: 15 mg/l; Sodium Pyruvate: 110.00 mg/l; L-Phenylalanine: 16.5 mg/l; L-Proline: 17.3 mg/l; L-Serine: 26.3 mg/l; L-Threonine: 17.9 mg/l; L-Tryptophan: 3.1 mg/l; L-Tyrosine 2Na $2H_2O$: 26.2 mg/l; L-Valine: 17.6 mg/l;

The present invention is also directed to a method of improving the pregnancy rate of a female undergoing in vitro fertilization, comprising the steps of: contacting an oocyte from said female with a monolayer of cultured human tubal epithelial cells; inseminating the oocyte; and transferring an embryo back to said female. Preferably, the human tubal epithelial cell are cultured according to the method as described above..

The instant invention teaches confluence (by definition >85% of surface is covered with cells) in 10 days. Prior art methods teach confluence in 4–7 days and this increase rate in confluence found is probably due to rapid fibroblast growth which cannot be considered to be the same as Applicants' culture conditions which highlight epithelial cell growth without fibroblast growth. The human embryo co-culture system of the present invention, due to quality control, culture conditions and modifications in serum is not obvious over the prior art.

This percent confluence was chosen because the cells were still actively dividing and not differentiating which would be the logical conclusion if one allowed the cells to teach confluence (i.e., >85% cell surface is covered with cells). By limiting the percent confluence, one encourages cell growth, not cell differentiation. The ability of the tubal cells to maintain their growing capacity, is important in the IVF coculture system, perhaps due to the growth factors generated during the stage of mitotic activity of the cells.

Prior art techniques have used CHANG MEDIUM® (6–8% FCS). Applicants used CHANG MEDIUM™ (6–8% FCS) with additional 5% fetal calf serum for the initial cell cultures (primary cell cultures). The amount of serum is critical for (1) the quality of the cultures, since these epithelial cells are actively mitotic in contrast to the differentiated ciliated cells of the prior art; (2) the quantity of the epithelial cell growth over any other cell type of growth; and to (3) provide factors which allow growth of epithelial cells without compromising the environment.

No second media has been used in any similiar prior art technique. Applicants have provided evidence that additional media sources (PC-I™) can be used after initial culturing. Low levels are maintained in the culture conditions which are far lower then provided in CHANG MEDIUM® used in prior art methods.

PC-I™ is serum free. This second media allows for the addition of a lower concentration of serum to be used after the initial cell culture conditions. The serum free media with additional concentrations of serum allows for the enhancement of epithelial cell growth while starving fibroblast growth. This clearly stabilized the tubal cell preparation and better simulated the conditions that the gametes/embryos would experience in vivo, i.e., ampullary tubal epithelial cells. However, serum still needs to be present in the culture media because the serum allows for cell attachment. No serum becomes detrimental to the passage and continuation of the cell. Therefore, lack of serum may not inhibit cell growth as much as it hinders cell attachment.

With regard to Applicants' method of improving the pregnancy rate of a female undergoing in vitro fertilization, Applicants note that prior art methods used pronucleated (i.e., fertilized, post-inseminated) embryos. Applicants have shown that earliest exposure of gametes (sperm and oocyte) to the tubal epithelial cells greatly enhance the embryo development over and above that of embryos alone. The tubal epithelial cells do not interfere with fertilization and this alone is novel and non-obvious over the prior art.

Furthermore, prior art methods generally used suspension of cells only. Applicants have shown otherwise and conclude that the coculture of oocytes and sperm on a layer of cells is more physiological to the condition that oocytes and sperm would experience in vivo, there would be an increased benefit to the development of the embryo and it does not interfere with fertilization.

Applicants respectfully note that embryos not gametes were used in the in vitro system of the prior art. At the ampullary junction, fertilization takes place. Since the cells isolated from the Fallopian tube is the ampullary portion of the tube, and since the purified cell culture is epithelial in origin, the environment which is simulated in vitro should be closer to the in vivo situation that the gametes would experience. This is to say that gametes should be allowed to fertilize, become embryos and grow and mature in the coculture setting, not just embryos. Prior art techniques describe a rapid transformation of oviductal cells to fibroblasts which is very common in classic culture conditions.

Applicants have described culture conditions which eliminate the rapid transformation of oviductal cells to fibroblasts. These modifications were made to enhance the epithelial cells.

The following examples are given for the purpose of illustrating various embodiments of the invention and are not meant to limit the present invention in any fashion.

EXAMPLE 1

Fallopian Tubes

Ampullary tubal segments from women undergoing postpartum sterilization were collected in 15 ml sterile Falcon tubes containing Hanks Balanced Salt Solution (HBSS, Gibco/BRL, Grand Island, N.Y.). Only tissue from patients with a negative screen for HIV, hepatitis B, syphilis, gonorrhea, and chlamydia were used. These experiments were reviewed and approved by the University of Alabama Institutional Review board.

EXAMPLE 2

Fallopian Tubal Cell Line

Ampullary tubal segments were washed in HBSS and placed in sterile petri dishes. The ampullary cells were scraped from inverted tubal segments into HBSS using fine forceps. The cell suspension was transferred to a 15 ml Falcon test tube and centrifuged. The media was removed and the primary cultures of tubal cells were resuspended in CHANG MEDIUM® A (Irvine Scientific; Irvine, Calif.) supplemented with antibiotics and antifungal agents and 5% fetal calf serum (FCS) (Qualified; Gibco/BRL, Grand Island, N.Y.). The tubal cells were plated in 75 $cm^3$ vented Falcon flasks (Becton Dickinson; San Jose, Calif.) at 37° C. in a 95% $O_2$/5% $CO_2$ humidified atmosphere until 60–70% confluence (7–10 days; primary culture). The cells were detached from the flasks with 0.5% trypsin +0.53 $\mu$M EDTA (Gibco/BRL, Grand Island, N.Y.) for 1 minute, the trypsin removed and the flask incubated at 37° C. in 95% $O_2$/5% $CO_2$ humidified atmosphere for 2 minutes. The cells were resuspended in 5 ml PC-I™ medium (Hycor; Irvine, Calif.) containing antibiotics and antifungal agents and 200 mM L-glutamine and centrifuged at 300 xg for 5 minutes. Two million cells were replated into four 75 $cm^3$ Falcon vented flasks containing PC-I™ medium/antibiotics/antifungal agents with either 5%, 10%, 20% or 40% fetal calf serum. When cells were 60–70% confluent, the medium was removed and the cells trypsinized, resuspended in fresh PC-I™ and fetal calf serum and seeded onto ethanol sterilized coverslips. After 5 days, the quality of the epithelial cells was determined. Analysis of cell morphology, immunohistochemistry and time of confluence was recorded after every subpassage of tubal cells.

EXAMPLE 3

Immunohistochemistry of Fallopian Tissue Sections and Tubal Cells

Archival Fallopian tubes from patients who underwent total hysterectomy (both luteal and follicular phase of menstrual cycle as determined by endometrial analysis) were sectioned at 5 $\mu$m, deparaffinized in xylene, rehydrated, and soaked in Tris-buffered saline for 10 minutes. The sections were stained by immunohistochemical methods. Tubal cells were fixed in neutral buffered formalin and dehydrated with sequential concentrations of ethanol, permeablized with acetone, rehydrated and soaked in Tris-buffered saline for 10 minutes. The cells were stained by immunohistochemical methods.

Tissue sections and tubal cells were treated with 3.0% aqueous hydrogen peroxide to quench endogenous peroxidase activity. The tissue/cells were incubated with preimmune rabbit serum for one hour to reduce non-specific staining. The tissue was subsequently incubated with cytokeratin, (Boehringer Mannheim, Indianapolis, Ind.) at a 1:100 dilution. A primary antibody in which mouse IgG was substituted for cytokeratin was used to examine specificity. The remainder of the immunohistochemical staining procedure was conducted using the Biogenex Z P000-WM Biotin-Streptavidine (B-SA) Detection System Horseradish Peroxidase Kit (Biogenex; San Ramon, Calif.) with diaminobenzidine tetrahydrochloride (DAB; Biogenex, San Ramon, Calif.) as substrate for visualization of antibody-antigen reactivity. The sections/cells were lightly counterstained with hematoxylin. Whole Fallopian tissue served as controls.

Cell morphology, immunohistochemistry and time to confluence (60–70%) were recorded. Quantification of immunohistochemical data was performed by two separate investigators who counted positively stained cells in 10 separate fields (×400 magnification).

EXAMPLE 4
Statistical Analysis

The relationship between serum concentration and epithelial cells proportion was analyzed by linear regression using the SAS/STAT statistical program.

EXAMPLE 5

Immunohistochemical analysis of intact human Fallopian tubes revealed that cytokeratin was consistently detected and localized (FIG. 1, Dark Arrow) in individual epithelial cells in the lumen of the Fallopian tube. This is the cell type which would come in direct contact with the gametes/embryos in the Fallopian tube. Interestingly, cytokeratin was not detected in any other cell type found in the Fallopian tube (FIG. 1, Open Arrow). Cytokeratin was detected in 90% of lumenal cells (epithelial cells) and was detected in all stages of the menstrual cycle (data not presented). Therefore, in the tubal cell cultures of the present invention, the growth and development of tubal epithelial cells in vitro was of paramount importance because this was the Fallopian tubal environment which came in contact with human gametes/embryos.

Figure 2:
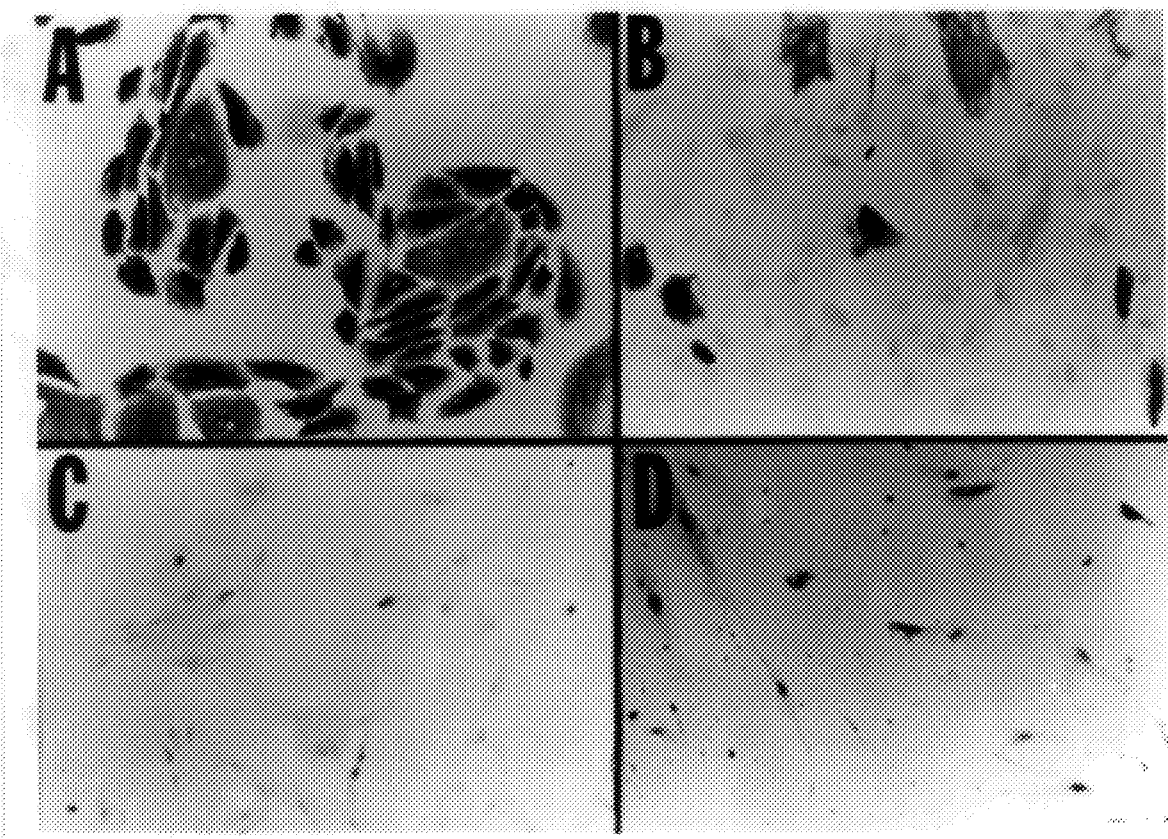
FIG. 2 shows the effect of serum concentration on tubal epithelial cell development. Cells from the same patient were cultured in media containing 5% (FIG. 2A), 10% (FIG. 2B), 20% (FIG. 2C) and 40% (FIG. 2D) fetal calf serum. After 4 passages, cells were stained for cytokeratin.
Figure 3:
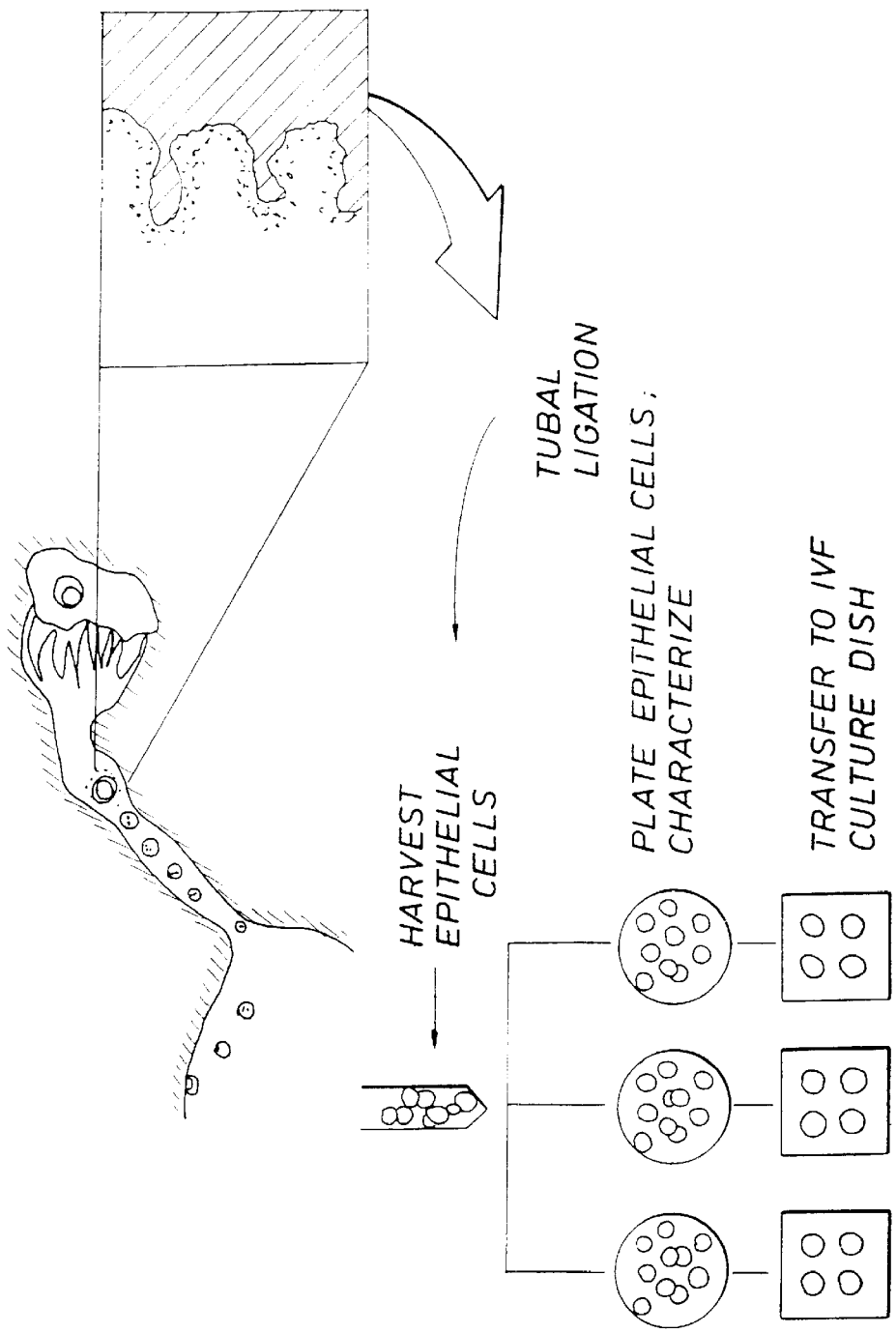
FIG. 3 shows a schematic of tubal epithelial cell harvest, epithelial cell characterization and in vitro fertilization co-culture preparation.
Figure 4:
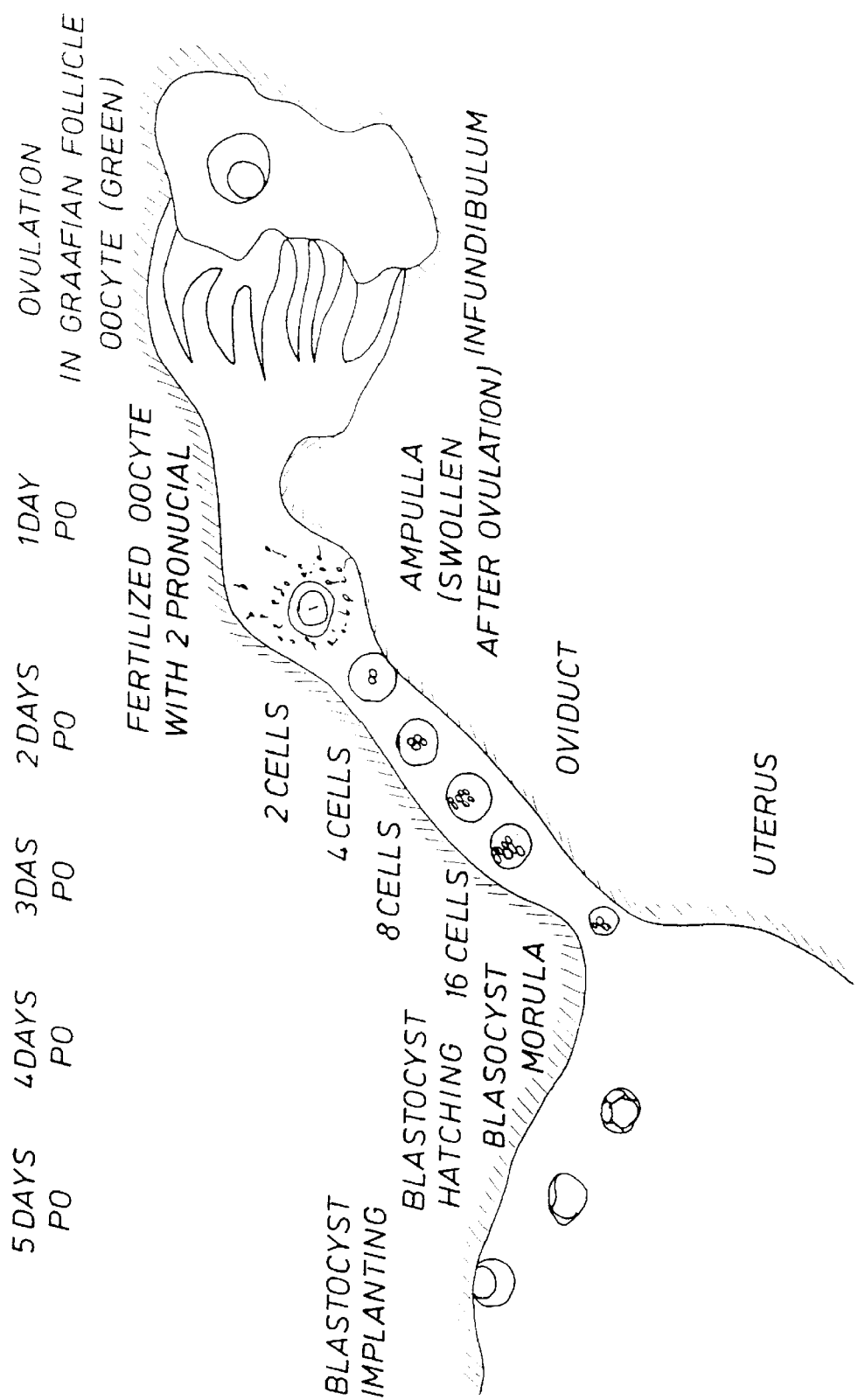
FIG. 4 shows a schematic of the regulation of embryo growth and development by tubal epithelial cells of the fallopian tube.

The concentration of serum added to the cultures of Fallopian tubal cells had a dramatic and unexpected effect on epithelial cell quantity and rate of development. Confluence rates were enhanced with increasing concentrations of FCS (Table 1) but this was at the expense of epithelial cell quantity (FIG. 2). Immunohistochemical data from tubal cells isolated from a single patient and passed 4 times clearly demonstrates that a dramatic negative correlation exists between serum concentrations and cytokeratin staining (FIG. 2).

TABLE I

Effect Of Heat Inactivation On The Ratio Of Epithelial Cells To Fibroblast Cells In Culture

| | Serum Concentrations | | | | |
|---|---|---|---|---|---|
| | 0% | 5% | 10% | 20% | 40% |
| Fetal Bovine Serum | | | | | |
| Epithelial Cells (%) | 47 ± 5 | 82 ± 5 | 66 ± 7 | 39 ± 3 | 4 ± 2 |
| Days to Confluence | >14 | 7 | 5 | 4.5 | 3 |

TABLE I-continued

Effect Of Heat Inactivation On The Ratio Of Epithelial Cells To Fibroblast Cells In Culture

| | Serum Concentrations | | | | |
|---|---|---|---|---|---|
| | 0% | 5% | 10% | 20% | 40% |
| Heat Inactivated Serum | | | | | |
| Epithelial Cells (%) | 47 ± 5 | 35 ± 7 | 42 ± 3 | 39 ± 7 | 37 ± 3 |
| Days to Confluence | >10 | >7 | 7 | 7 | 7 |

EXAMPLE 6

There have been conflicting reports and much 5 disagreement in the art (See, e.g., Bongso et al., *J In Vitro Fertilization Embryo Transfer*,1991, 8:216–221; Menezo et al., *Biol Reprod,*1990; 42:301–306; Bongso et al., *Hum Reprod.* 1989; 4:706–713; Sathananathan et al., *Hum Reprod.,*1990, 5:309–318; Wiemer et al., *Hum. Reprod,* 1989, 4:595–600; Yeung et al., Hum Reprod 1992, 7:1144–1149; Van Blerkom, *Human Reprod,* 1993, 8:1525–1539; and Bavister et al., *Hum. Reprod,* 1992, 7:1339–1341) as to whether gametes/embryos which are co-cultured with various cell-types have better fertilization rates and morphology then those gametes/embryos which were not. In light of these controversial findings and the lack of characterization of many of the cell types reported in the literature, the present invention demonstrates the importance of one specific aspect of tubal cell propagation, namely the effect of serum concentrations on human tubal cell growth and development. The present invention clearly shows that the use of low serum concentrations for tubal cell propagation favors the growth of epithelial cells over fibroblasts.

It has been observed that tubal cells, when cultured in vitro, change appearance from a typical epithelial cell morphology (cobblestone appearance) to a typical fibroblastic cell morphology (long, slender appearance. The reason for this often sudden change in morphology has many investigators concerned of the consequences of using this "fibroblastic" cells in their co-culture conditions and question the reason for such sudden morphological changes. It has been suggested that the best co-culture effects are from early cell generations. The reason for concern may be due to the limited amount of characterization of these cells and the culture conditions which these cells are exposed. The morphology of tubal epithelial cells can be enhanced or inhibited by the culture conditions from which they are derived, namely the serum composition of the culture medium. This alteration in growth and morphology of the tubal cells (either fibroblasts or epithelial cells) could be reflected in the conflicting effects of the co-culture system on embryo morphology. In addition, reports of differential expressions of growth factors produced by epithelial and non-epithelial cells of the Fallopian tube could alter the results of embryo co-culture systems.

Some investigators have suggested using early subpassaged cells in co-culture of gametes/embryos due to their cobblestone appearance and presumed epithelial origin. Others have reported using cells after 25 subpassaged with success but noted their fibroblastic cell formation. The importance of an epithelial or fibroblastic cell morphology and its beneficial role in embryo co-culture was unclear. If the goal of designing a co-culture system, however, is to mimic the Fallopian tube in vitro, it is beneficial to promote the growth of epithelial cells since these cells are in direct contact with the pre-implantation embryo in vivo.

EXAMPLE 7
Gamete/Embryo Co-culture Using Fresh or Frozen Homologous Tubal Cells On Human IVF And Preimplantation Embryo Development As shown above, co-culture of human gametes/preimplantation embryos with homologous tubal cells improved embryo development and morphology. The effects of using frozen/thawed vs nonfrozen human tubal cells for gamete/embryo coculture was also shown. The design comprised a randomized controlled trial involving infertile women undergoing IVF (n=14) or gamete intrafallopian transfer (GIFT) (n=24).

A co-culture system was employed using tubal ampullary cells obtained from surgical specimens of women undergoing post-partum tubal sterilization. Tubal cells ($10^5$) were plated onto 4-well Nunc dishes 24 hours prior to egg retrieval. All oocytes of women undergoing IVF and all spare oocytes of women undergoing GIFT were randomly assigned to either nonfrozen or previously frozen and thawed tubal cells with HTF media and 0.5% BSA. The two groups were compared for the rates of fertilization, embryo cleavage, blastomere number and embryo morphology. Embryo morphology was scored 44 hours after insemination based on the degree of blastomere symmetry and fragmentation.

A total of 333 oocytes were randomized (168 nonfrozen, 165 frozen). Passage number of the fresh cell line was significantly lower than the frozen (fresh 3.0, frozen 4.96; P=0.0001). However, fertilization rates were not significantly different (nonfrozen 48.2%, frozen 47.9%; p=0.95). Complete failure of fertilization was encountered in one IVF patient. Among the fertilized eggs, the proportions that cleaved were similar (fresh 92.6%, frozen 96.2%; p=0.495). There were no significant differences among the mean number of blastomeres (nonfrozen 2.89; frozen 2.82; p=0.60) or average morphology scores of the embryos (nonfrozen 5.91; frozen 5.82; p=0.48). Among IVF patients, embryos were no more likely to be chosen for transfer from either the fresh or frozen co-culture system (p=0.917). There was no association between the passage number of the cell line and either the embryo morphology score ($R^2=0.01$; p=0.36) or the number of blastomeres ($R^2=0.02$; p=0.25) observed at 44 hours after insemination. Among 13 patients who underwent embryo transfer, six (46%) achieved a clinical pregnancy, with 7 gestational sacs visualized (12.5% implantation rate). Thus, freezing and thawing human tubal cell lines does not reduce the beneficial effect on embryo development and morphology when compared to nonfrozen cell lines. Within the first seven cell line passages, there appears to be no diminution of co-culture benefit with increasing pass number.

EXAMPLE 8
Effects Of Gamete/Embryo Co-culture Using Homologous Tubal Cells On Human IVF And Preimplantation Embryo Development Co-culture of pre-implantation embryos with cells derived from the reproductive tract enhances embryo development. The prior art studies employed co-culture only after fertilization had been observed, in part because of presumed adverse interactions between co-culture feeder cells and spermatozoa. The effects of the exposure of human eggs and sperm to human tubal cell co-culture on fertilization and embryo development are shown along with the beneficial effects of embryo co-culture using a standard serum-free IVF culture medium.

Randomized controlled trial involving 16 infertile women undergoing IVF or GIFT. A co-culture system was designed using tubal endothelial cells obtained from surgical specimens of women undergoing post-partum tubal sterilization. Tubal cells ($10^5$) were plated onto 4-well Nunc dishes 24 hours before egg retrieval. All oocytes of women undergoing IVF and all spare oocytes of women undergoing GIFT were randomly assigned to either conventional culture with Human Tubal Fluid+0.5% BSA or human tubal cell co-culture using the same medium. The two groups were compared for the rates of fertilization and embryo cleavage, and the culture media were examined for sperm motility at 24 and 44 hours after insemination. An embryo morphology score based on the degree of blastomere symmetry and fragmentation was assigned at 44 hours after insemination.

A total of 249 oocytes were randomized (122 co-culture, 127 standard culture). Fertilization rates were not significantly different (co-culture: 61%, Standard: 60%; p=0.896). Among the fertilized eggs, 97% in co-culture cleaved, while 95% in standard culture cleaved (p=0.424). The number of blastomeres apparent at 44 hours was not significantly different (co-culture: 2.9, Standard: 2.7; p=0.1787). However, the morphology of co-cultured embryos was significantly better than those in standard culture (Morphology-score co-culture: 3.3, Standard: 2.9; p=0.0001). In patients not undergoing GIFT, the best quality embryos were chosen for transfer; embryos obtained from co-culture were more likely to be chosen for transfer than those in standard culture (co-culture: 66.7%, Standard: 46.7%; p=0.056). Of 33 embryos transferred to study participants in whom the treatment cycle outcomes are known thus far, 7 gestational sacs have been documented (implantation rate=21 %). Thus, co-culture of human eggs and sperm with homologous tubal cells does not affect fertilization. The beneficial effect on embryo development is primarily manifested by an improvement in embryo morphology and is not obviated by use of a serum-free medium. The clinical results illustrate that this culture system is associated with high implantation rates.

EXAMPLE 9
Effect Of Gamete/Embryo Coculture With Human Tubal Cells On In Vitro Fertilization Success The effects of gamete/embryo co-culture using homologous tubal cells on pregnancy rates with human in vitro fertilization was demonstrated. A co-culture system was designed using tubal endothelial cells obtained from surgical specimens of women undergoing postpartum tubal sterilization. Tubal cells ($10^5$) were plated onto 4-well Nunc dishes 24 hours before egg retrieval. Oocytes of women undergoing in vitro fertilization were cultured over the tubal cell monolayer over Human Tubal Fluid (HTF)+0.5% bovine serum albumin (BSA) beginning immediately after retrieval, and insemination was performed 4 to 6 hours later. Embryo transfer was performed 2 days after egg retrieval. The results of IVF cycles in the twelve months after introduction of co-culture were compared with the cycles performed during the 36 months immediately prior to development of the co-culture system.

One hundred twenty-one cycles with standard culture media (S) were compared with 39 cycles using co-culture (C). The distributions of infertility diagnoses in the two patient groups were similar. The two patient groups had similar ages (Standard culture: 33.8 yrs, Co-culture: 33.7 yrs; p=0.9), numbers of egg retrieved (Standard culture: 11.9, Co-culture: 14.3; p=0.09), fertilization rates (Standard culture: 55%, Co-culture: 60%; p=0.34) and numbers of embryos transferred (Standard culture: 4.3, Co-culture: 4.9; p=0,17). The clinical pregnancy rate per retrieval was significantly higher in the co-culture group (Standard culture: 16.5%, Co-culture: 30.8%; P=0.05). Thus, the present invention demonstrates that co-culture of human eggs and sperm with homologous tubal cells does not affect fertilization rates in vitro but improves pregnancy rates in patients undergoing IVF.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A human embryo co-culture system comprising a suspension of cultured human tubal epithelial cells, wherein said human tubal epithelial cells are cultured by the steps of:
   culturing ampullary cells in a container holding a first medium until about 40% to about 80% confluence, wherein said first medium is CHANG MEDIUM® A supplemented with fetal calf serum, antibiotics and antifungal agents;
   detaching said cells from the surface of said container; and
   resuspending said cells in PC-I™ medium with serum, antibiotics and antifingal agents and replating said cells until about 40% to abut 80% confluence.

2. The human embryo co-culture system of claim 1, wherein said suspension is frozen.

3. The human embryo co-culture system of claim 1, wherein said cells are cultured in PC-1™ medium until about 60% to about 70% confluence.

4. The human embryo co-culture system of claim 1, wherein said cells are detached from said container manually.

5. The human embryo co-culture system of claim 1, wherein said cells are detached from said container chemically.

6. The human embryo co-culture system of claim 5, wherein said cells are detached from said container by treating said cells with trypsin.

7. The human embryo co-culture system of claim 1, wherein said serum is selected from the group consisting of fetal calf serum, bovine serum and female donor serum.

8. The human embryo co-culture system of claim 7, wherein said fetal calf serum is in a concentration of about 1% to about 10%.

9. The human embryo co-culture system of claim 8, wherein said fetal calf serum is in a concentration of about 5%.

10. The human embryo co-culture system of claim 1, wherein said antibiotics are selected from the group consisting of penicillin and streptomycin.

11. The human embryo co-culture system of claim 1, wherein said antifungal agent is amphotericin B.

12. A method of improving the pregnancy rate of a female undergoing in vitro fertilization, comprising the steps of:
   contacting an oocyte from said female with a monolayer of cultured human tubal epithelial cells of claim 1;
   inseminating the oocyte; and
   transferring an embryo back to said female.

* * * * *